United States Patent
Eaton

(10) Patent No.: US 9,814,839 B2
(45) Date of Patent: Nov. 14, 2017

(54) AUTOINJECTOR DEVICE

(75) Inventor: Mark Eaton, Witney (GB)

(73) Assignee: OWEN MUMFORD LIMITED, Oxford (GB)

( * ) Notice: Subject to any disclaimer, the term of this patent is extended or adjusted under 35 U.S.C. 154(b) by 745 days.

(21) Appl. No.: 14/007,093

(22) PCT Filed: Mar. 26, 2012

(86) PCT No.: PCT/GB2012/050660
§ 371 (c)(1),
(2), (4) Date: Oct. 23, 2013

(87) PCT Pub. No.: WO2012/127249
PCT Pub. Date: Sep. 27, 2012

(65) Prior Publication Data
US 2014/0046269 A1    Feb. 13, 2014

(30) Foreign Application Priority Data

Mar. 24, 2011    (GB) .................................. 1104957.4

(51) Int. Cl.
*A61M 5/315* (2006.01)
*A61M 5/20* (2006.01)
A61M 5/32 (2006.01)

(52) U.S. Cl.
CPC ...... *A61M 5/31505* (2013.01); *A61M 5/2033* (2013.01); *A61M 5/3204* (2013.01); *A61M 2005/206* (2013.01); *A61M 2005/208* (2013.01)

(58) Field of Classification Search
CPC ...... A61M 2005/206; A61M 2005/208; A61M 5/2033; A61M 5/31505; A61M 5/3204
See application file for complete search history.

(56) References Cited

U.S. PATENT DOCUMENTS 5,320,609 A * 6/1994 Haber ................. A61M 5/2033
604/135
2003/0105430 A1    6/2003 Lavi
(Continued)

FOREIGN PATENT DOCUMENTS

WO    94/21316    9/1994
WO    96/24398    8/1996
(Continued)

OTHER PUBLICATIONS

International Search Report dated Sep. 4, 2012; corresponding to PCT/GB2012/050660.
(Continued)

*Primary Examiner* — Imani Hayman
(74) *Attorney, Agent, or Firm* — Young & Thompson

(57) ABSTRACT

An autoinjector device includes an elongate housing containing a syringe or cartridge having an internal piston for expressing a dose from the syringe or cartridge. A drive mechanism includes a drive member engaging the piston and a drive spring acting on the drive member. A side-operated trigger arrangement includes a retention element movably mounted in the housing from a retaining position in which the drive member is kept in a cocked condition, and a release position in which the drive member may more forwardly under spring pressure. An outer sleeve is mounted on the housing movable between a position in which the retention element is prevented from moving to release the plunger, and a position in which the retention member moves freely. The outer sleeve includes a trigger wall portion which may be depressed to move the retention element once the retention element is free to move, releasing the plunger.

20 Claims, 5 Drawing Sheets

(56) References Cited

U.S. PATENT DOCUMENTS

2006/0224124 A1 10/2006 Scherer
2006/0270984 A1 11/2006 Hommann

FOREIGN PATENT DOCUMENTS

| WO | 97/48430 | 12/1997 |
|----|----------|---------|
| WO | 03/097133 | 11/2003 |
| WO | 2007/036676 | 4/2007 |
| WO | 2010/037759 | 4/2010 |

OTHER PUBLICATIONS

British Search Report dated Jul. 20, 2011; Corresponding to the Foreign Priority Application No. GB 1104957.4.

\* cited by examiner

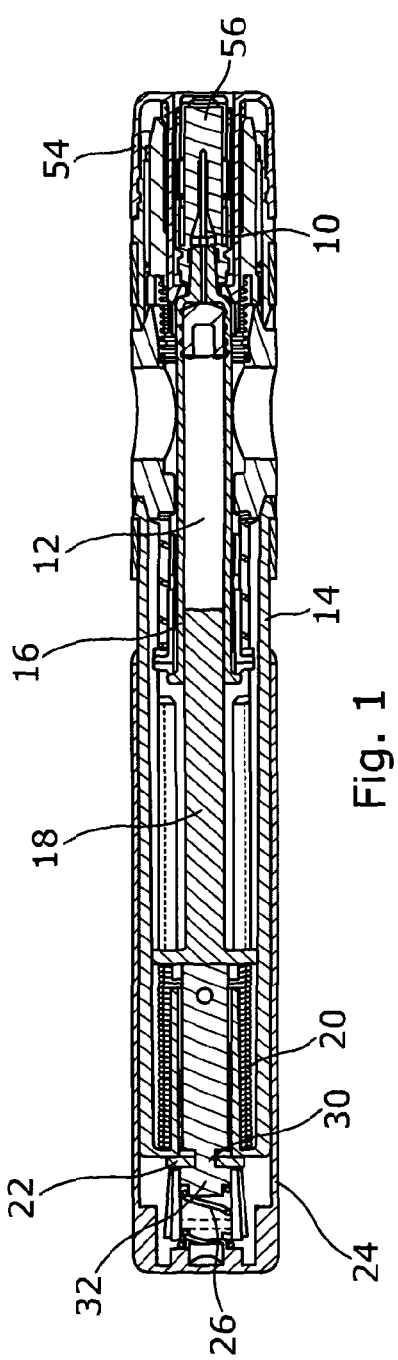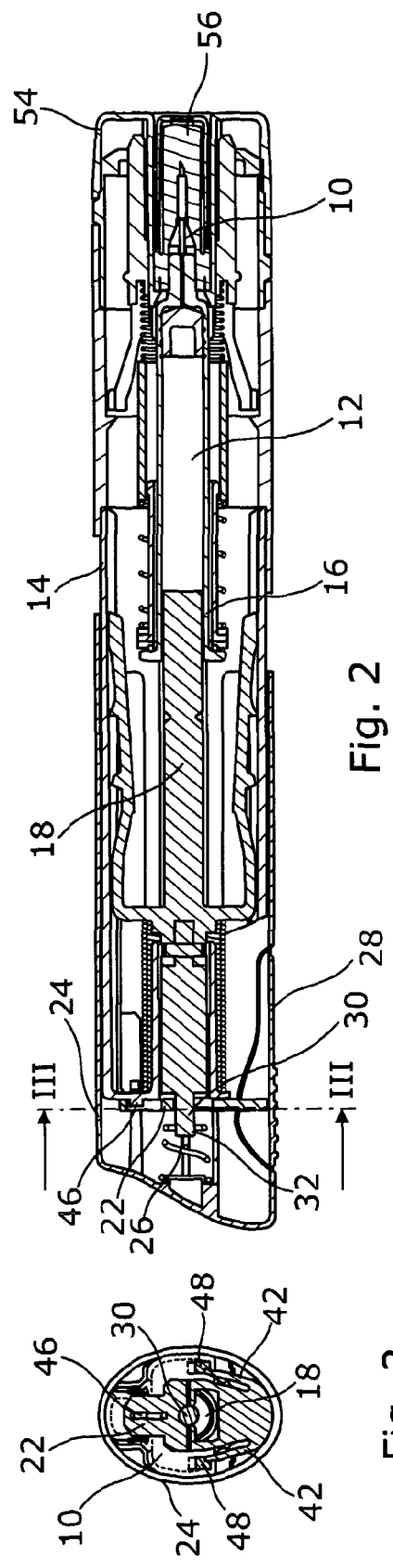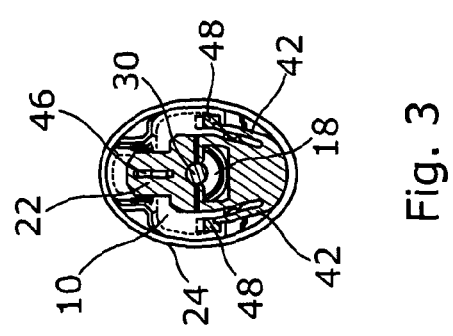

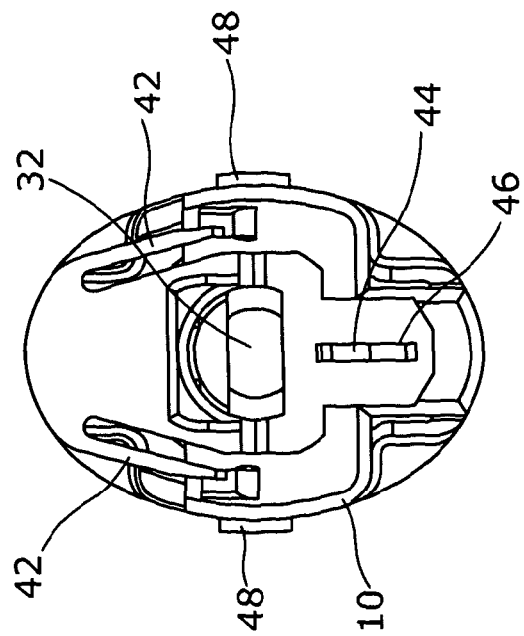
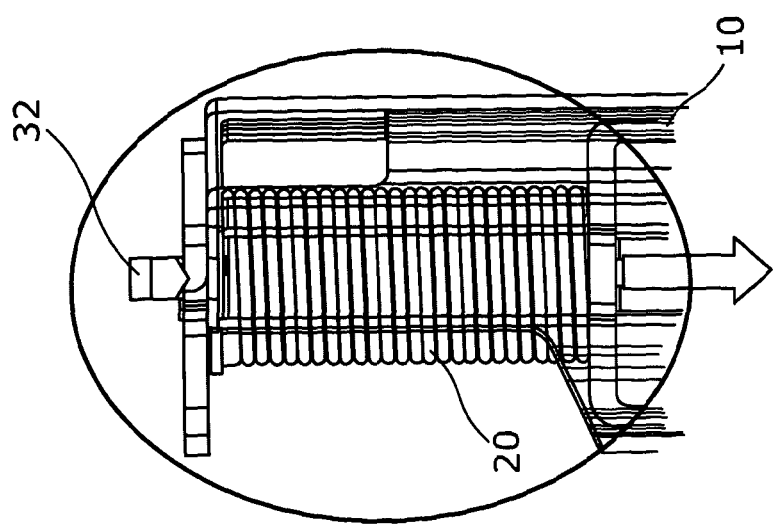
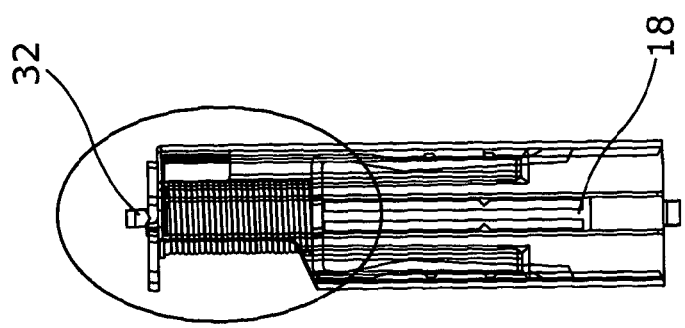
Fig. 5(c)
Fig. 5(b)
Fig. 5(a)

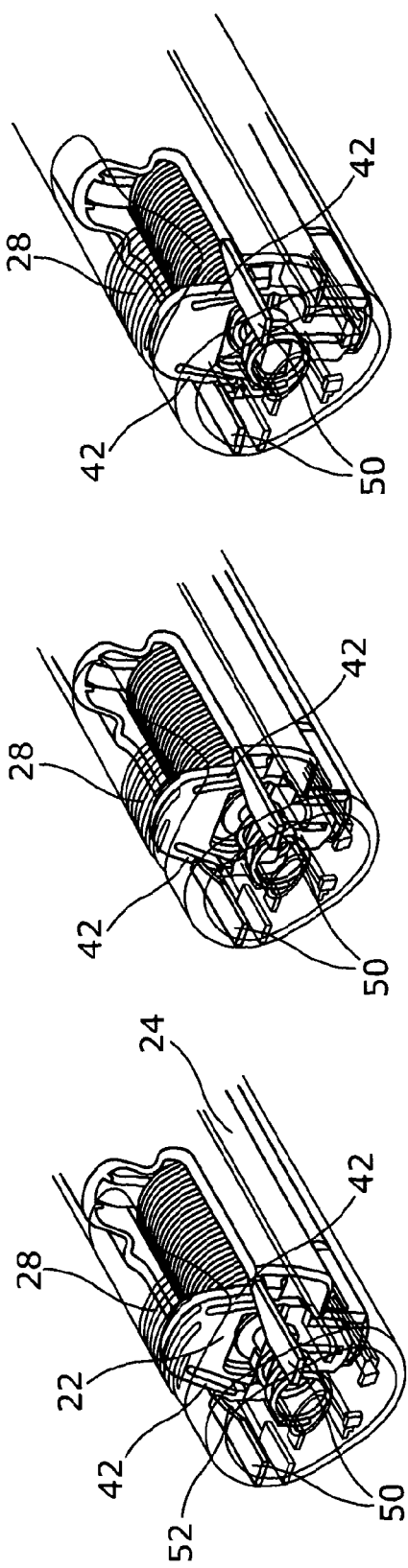

AUTOINJECTOR DEVICE

This invention relates to autoinjector devices having a drive mechanism including a trigger arrangement operable to release a plunger to move forwardly relative to the device to expel a dose.

In our earlier publication WO94/21316 we disclose an arrangement in which a sleeve is slideably mounted on the rear end of the autoinjector housing, and has an aperture through which a laterally facing trigger is exposed. The trigger is hingeably mounted by live hinges to the main housing and has latch hooks which latch the drive plunger of the device against forward movement, with the hooks and trigger thereby reacting the load of the compressed drive spring. The external sleeve can be moved against a spring bias from a safe position in which it inhibits operation of the trigger, and an armed position in which the trigger may be operated to release the plunger. Although this design has proved extremely successful in practice, particularly for reusable devices, the present inventors have developed certain improvements.

In particular, in the above design, the trigger reacts the drive load when the device is cocked, and this places significant design constraints on the trigger. We have therefore designed a side actuated mechanism in which the load of the drive spring when the device is cocked is reacted by a separate reaction element. Although usable in autoinjectors in general, this feature is particularly appropriate for single use autoinjectors that are supplied in a cocked condition and in which the retention element is therefore under load for many months or years. Also, in the prior art arrangement, mounting the manually operable trigger on the housing means that a large aperture has to be provided in the sleeve which is undesirable.

Accordingly, in one aspect, this invention provides an autoinjector device comprising:

an elongate housing containing a syringe or cartridge having an internal piston for expressing a dose from the syringe or cartridge, a drive member for engaging said piston, and a drive energy source acting on said drive member;

a retention member movably mounted with respect to said housing for movement between a retaining position in which the drive member is kept in a cocked condition with the drive energy source energised, and a release position in which the drive member is free to move under the influence of the drive source, and an outer sleeve movably mounted with respect to said housing, said outer sleeve having associated therewith a trigger element movable to urge said retention member and to move it to its release position, and the outer sleeve being movable between a safe state in which said retention member is prevented from moving to its release position, and a ready state in which the retention member is free to move to its release position when urged by action of said trigger element.

In the above arrangement the trigger element may form part of the outer sleeve rather than the housing. This means that the trigger element may form integrally with the outer sleeve, without requiring a separate aperture. Furthermore, the retention member carries the load on the plunger when cocked, and the trigger element itself is not subject to load when the device is cocked.

Conveniently said retention member and said housing have respective cooperating abutments at least one of which is resiliently movable between a safe position in which movement of said retention element to said release position is prevented, and a ready position in which movement is allowed. In this case, movement of said sleeve from its safe to its ready state preferably causes said resiliently movable abutment to move to its ready position. Such movement may be achieved by providing the sleeve with a surface for engaging said resilient abutment. Thus said surface may be a camming surface.

Whilst the invention has been described above, it extends to any invention combination of the features set out above or in the following description or drawings.

The invention may be performed in various ways and, by way of example only, an embodiment thereof will now be described, with reference to the accompany drawings, in which:

FIG. 1 is a horizontal longitudinal section view through an embodiment of an autoinjector in accordance with this invention;

FIG. 2 is a vertical section view through the embodiment of FIG. 1;

FIG. 3 is a transverse section view taken on rows III-III of FIG. 2;

Figure 4A:
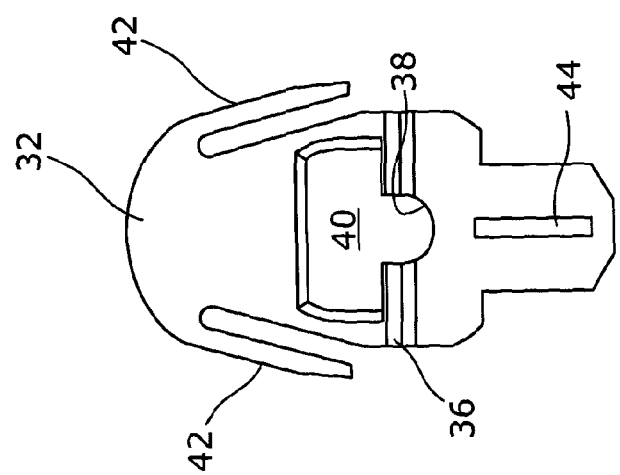
Figure 4B:
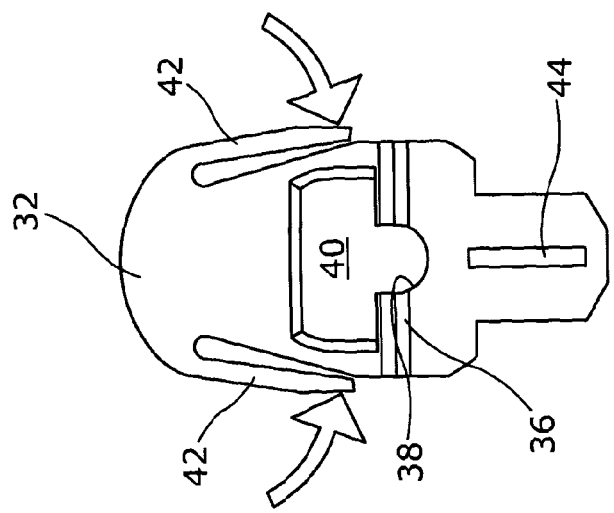
Figure 4C:
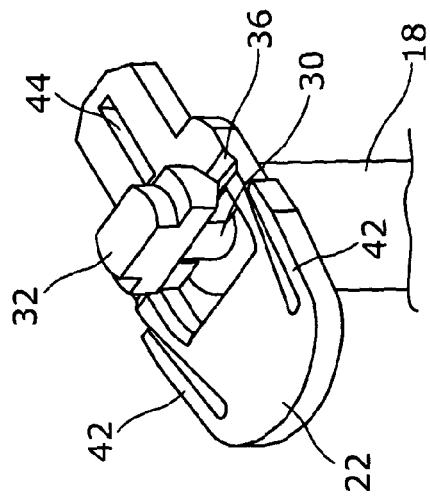
Figure 4D:
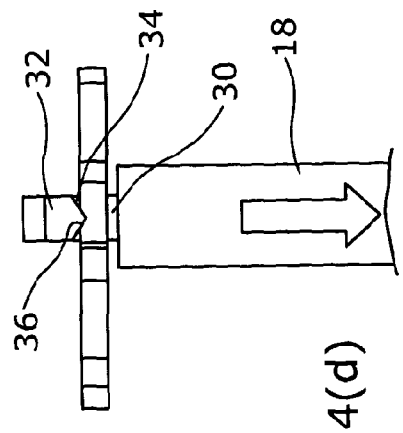
Figure 7C:
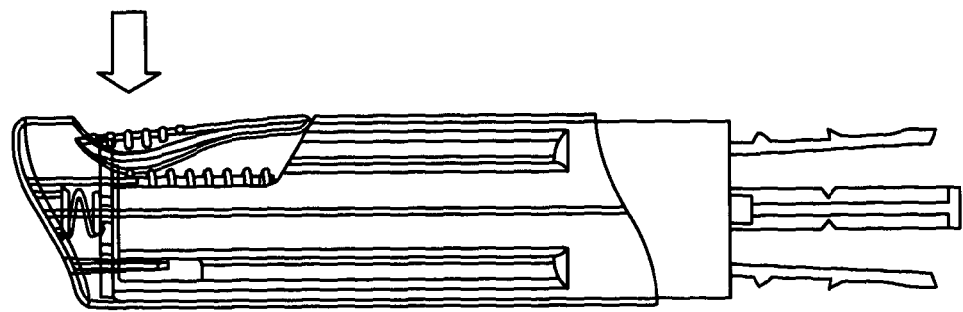
Figure 7B:
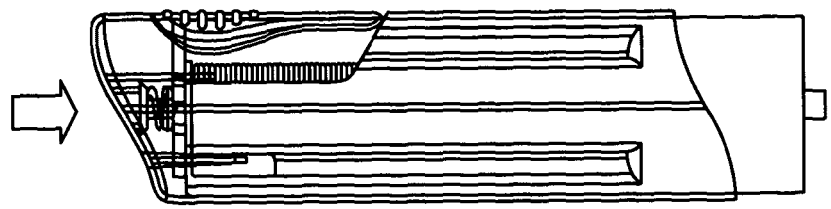
Figure 7A:
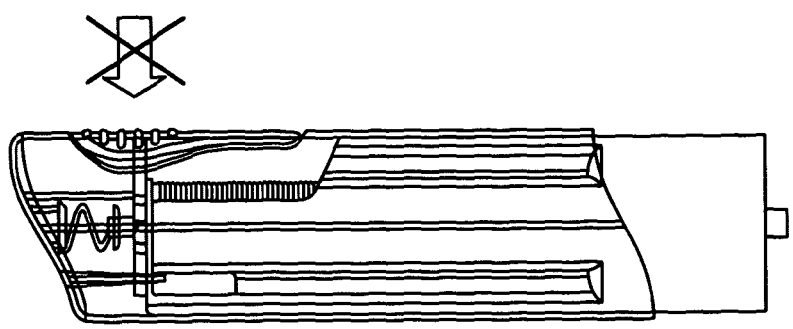

FIGS. 4(*a*) to (*d*) are views of the plunger retention element of the embodiment of FIGS. 1 to 3 viewed on an enlarged scale in a relaxed, safe state, a compressed armed state, and in perspective and side view respectively showing interaction of the retention member with the plunger;

FIGS. 5(*a*), (*b*) and (*c*) are detailed views on the rear end of the drive assembly showing interaction of the retention plate with the plunger in side view, an enlarged detail and a top view respectively;

FIGS. 6(*a*), (*b*) and (*c*) are detailed views on the rear end of the autoinjector with the sleeve in its rest, intermediate and forward positions respectively, showing movement of the plunger retention element from its relaxed, safe state to its compressed, armed state; and showing the sleeve as transparent, with FIGS. 6(*d*) to (*f*) being enlarged detailed items on FIGS. 6(*a*) to (*c*), and FIGS. 7(*a*), (*b*) and (*c*) are side views on the rear end of the autoinjector in its rest, intermediate and forward positions, with the sleeve shown in transparent.

Referring initially to FIGS. 1 to 3, the embodiment of autoinjector this invention comprises an outer housing 10 containing a syringe 12 with a needle 14 mounted in a syringe carrier 16 for forward movement. A drive plunger 18 is shown latched in a cocked position against the force of a main drive spring 20. The drive plunger is releasably held in its cocked position by means of a retention plate 22 e.g. of plastics material. Slideably mounted on the outside of the housing 10 is an external sleeve 24 which is biased rearwardly by a sleeve spring 26. When the sleeve 24 is shifted forwardly on the housing, a trigger 28 may be pressed inwardly to shift the retention plate 22 to release the plunger thereby extending the syringe and expelling a dose.

Referring now more particularly to FIGS. 3 and 4, and to the trigger mechanism, the drive plunger has at its rear end a reduced diameter neck 30 topped by a head 32 to form a T-shape as seen more particularly in FIGS. 4(*c*) and (*d*). The head 32 has V-shaped contact surfaces 34 that seat in a plunger indexing rebate 36 in the retention plate 22 when the device is cocked. The retention plate has a D-shaped plunger retaining aperture 38 which merges with an enlarged plunger release opening 40. Two resilient integral latch arms 42 extend from one side of the plate down its sides. A slot 44 is provided to cooperate with a peg 46 on the housing to constrain movement of the retention plate. The outer housing 10 also includes two abutments 48 that cooperate with the latch arms 42 on the retention plate 22 to prevent movement of the retention plate between its retaining position (as shown in FIGS. 1 to 3) and its release position, where the plunger 18 is released for forward movement.

Internally of the rear end of the sleeve 24 are two spaced de-latching elements 50 having inclined forward camming surfaces 52. These de-latching elements are best seen in FIGS. 6(a) to (f) and are designed to cooperate with and squeeze the latch arms 42 against the sides of the retention plate 22 to release them from engagement with the abutments 48, when the sleeve 24 is shifted forwardly on the housing. Once the latch arms 42 are clear of the abutments, the retention plate 22 can be shifted to release the plunger when the trigger wall portion 28 is pressed inwardly.

Thus, in operation, a user will prepare the autoinjector by removing a cap 54 at the front end thereby also removing a needle shield 56 and preparing the device for injection. The device is then offered up to an injection site, with the front end placed in contact with the skin around the injection site. The sleeve 24 in the pressed so that it shifts forwardly on the outer housing with the de-latching elements 50 squeezing the latch arms 42 clear of the abutments 48, as seen in sequence in FIGS. 6(a) to (f) and 7(a), (b) and (c). When the user is ready, they press the trigger wall portion 28 inwardly, thereby shifting the retention plate 22 so that it releases the drive plunger 18 so that it shoots forwardly under the influence of the drive spring 20.

In this arrangement, the drive spring load is taken by the retention plate which itself is separate from the trigger. This means that the trigger wall portion does not have to sustain the load of the drive spring and can be of lighter construction. A further advantage is that, in the arrangement as described, the restraining load provided by the retaining plate is symmetric about the longitudinal axis of the plunger and so the retention forces are balanced.

The invention claimed is:

1. An autoinjector device comprising:
   an elongate housing (10) containing
   a syringe or cartridge (12) having an internal piston for expressing a dose from the syringe or cartridge,
   a plunger member (18) for engaging said piston, and
   a drive energy source (20) acting on said plunger member (18);
   a retention member (22) moveably mounted in said housing and movable between
   i) a retaining position in which the retention member engages the plunger member (18) to keep the plunger member in a cocked condition with the drive energy source (20) energized, and
   ii) a release position in which the plunger member (18) is disengaged to release the plunger member for movement under the influence of the drive source;
   the autoinjector device further comprising:
   an outer sleeve (24) axially slidably mounted with respect to said housing (10),
   said outer sleeve (24) having associated therewith a trigger element (28) movable to urge said retention member to move to said release position, and
   the outer sleeve (24) being axially movable between
   i) a rearward safe state position in which said retention member (22) is prevented from moving to said release position, and
   ii) a forward ready state position in which the retention member (22) is free to move to said release position when urged by action of said trigger element (28),
   wherein the outer sleeve is rearwardly biased relative to the housing towards the safe state position, and
   wherein in use the outer sleeve moves forwardly on the outer housing against said rearward bias from the safe state position to the ready state position when a forward end of the autoinjection device is urged against an injection site such that the retention member is free to move to said release position when urged by action of said trigger element.

2. The autoinjector device according to claim 1, wherein said retention member (22) and said housing (10) have respective cooperating abutments (42, 48) at least one of which is a resiliently movable abutment (42) resiliently movable between the safe position in which movement of said retention element to said release position is prevented, and the ready state position in which movement of said retention element to said release position is allowed.

3. The autoinjector device according to claim 2, wherein movement of said outer sleeve (24) from said safe state position to said ready state position causes said resiliently movable abutment (42) to move to said ready state position.

4. The autoinjector device according to claim 3, wherein said outer sleeve (24) includes a surface (50) for engaging said resiliently movable abutment (42).

5. The autoinjector device according to claim 4, wherein said surface (50) is a camming surface.

6. The autoinjector device according to claim 2, wherein said retention member (22) and said housing (10) each have two abutments which cooperate with abutments on the other thereof.

7. The autoinjector device according to claim 1, wherein said trigger element (28) comprises a trigger wall portion formed integrally with said outer sleeve (24).

8. The autoinjector device according to claim 1, wherein said retention member (22) is mounted for transverse sliding movement relative to the housing (10).

9. The autoinjector device according to claim 1, wherein said retention member (22) includes a plunger retaining aperture (38) for receiving a necked portion (30) of said plunger member (18) to retain said plunger member, and a plunger release opening (40) merging with said plunger retaining aperture, through which the necked portion may pass when said retention member is in said release position.

10. The autoinjector according to claim 9, wherein said plunger member (18) is elongate with an enlarged head (32) with contact surfaces (34) spaced to either side of the longitudinal axis which engage corresponding surfaces (36) in the plunger retention member.

11. The autoinjector according to claim 10, wherein said contact surfaces (34) are diametrically aligned relative to said longitudinal axis.

12. The autoinjector device according to claim 3, wherein said retention member (22) and said housing (10) each have two abutments which cooperate with abutments on the other thereof.

13. The autoinjector device according to claim 4, wherein said retention member (22) and said housing (10) each have two abutments which cooperate with abutments on the other thereof.

14. The autoinjector device according to claim 2, wherein said trigger element (28) comprises a trigger region formed integrally with said outer sleeve (24).

15. The autoinjector device according to claim 3, wherein said trigger element (28) comprises a trigger wall portion formed integrally with said outer sleeve (24).

16. The autoinjector device according to claim 4, wherein said trigger element (28) comprises a trigger wall portion formed integrally with said outer sleeve (24).

17. The autoinjector device according to claim 5, wherein said trigger element (28) comprises a trigger wall portion formed integrally with said outer sleeve (24).

18. The autoinjector device according to claim 6, wherein said trigger element (28) comprises a trigger wall portion formed integrally with said outer sleeve (24).

19. The autoinjector as claimed in claim 1, wherein the outer sleeve extends over and surrounds a rearward portion of the housing to provide an outer surface which the user grips to urge the device against an injection site.

20. The autoinjector as claimed in claim 1, wherein the trigger element is an integrally formed part of the outer sleeve, and the retention member carries a load of the drive energy source (20) acting on the plunger member when the retention member is in the retaining position, and the trigger element is not subject to said load when the retention member is in the retaining position.

* * * * *